United States Patent [19]

Yoneyama et al.

[11] Patent Number: 5,550,226
[45] Date of Patent: Aug. 27, 1996

[54] SACCHARIDE IN THE FORM OF POWDER, AND ITS PREPARATION AND USE

[75] Inventors: Masaru Yoneyama; Takashi Shibuya; Toshio Miyake, all of Okayama, Japan

[73] Assignee: Kabushiki Kaisha Hayashibara Seibutsu Kagaku Kenkyujo, Okayama, Japan

[21] Appl. No.: 316,372

[22] Filed: Oct. 3, 1994

Related U.S. Application Data

[63] Continuation of Ser. No. 894,482, Jun. 5, 1992, abandoned.

[30] Foreign Application Priority Data

Jun. 6, 1991 [JP] Japan .................. 3-233646

[51] Int. Cl.$^6$ .............. C13K 13/00; C13K 1/08; C07H 3/06
[52] U.S. Cl. ................ 536/123.13; 536/123.1; 536/124; 536/127; 514/54; 424/493
[58] Field of Search .............. 536/123.13, 123.1, 536/124, 127; 514/54; 424/493

[56] References Cited

U.S. PATENT DOCUMENTS

| | | | |
|---|---|---|---|
| 3,619,292 | 11/1971 | Brouillard et al. | 127/29 |
| 4,518,581 | 5/1985 | Miyake et al. | 424/48 |
| 4,595,418 | 6/1986 | Yoshino | 127/30 |
| 4,843,156 | 6/1989 | Miyake et al. | 536/127 |
| 4,871,840 | 10/1989 | Kobayashi et al. | 536/103 |
| 4,975,535 | 12/1990 | Masai et al. | 536/124 |
| 5,112,407 | 5/1992 | Sakai et al. | 127/58 |

FOREIGN PATENT DOCUMENTS

| | | |
|---|---|---|
| 6030695 | 2/1985 | Japan . |
| 219345 | 9/1986 | Japan . |
| 1171493 | 7/1989 | Japan . |
| 5876063 | 5/1993 | Japan . |
| WO90/06317 | 6/1990 | WIPO . |

OTHER PUBLICATIONS

WOLFROM et al; *A Chemical Synthesis of Panose and an Isometric Trisaccharide*; THE JOURNAL OF ORGANIC CHEMISTRY; vol. 32; No. 3; Mar. 1967.

The Journal of Biological Chemistry, vol. 200, pp. 793–801 (1953), "Enzymatic Synthesis of Dextran Acceptor Specificity and Chain Initiation"; Koepsell et al.

Journal of the American Chemical Society, vol. 77, pp. 3315–3318, (1955); "Preparation of Panose by the Action of NRRL B–512 Dextransucrase on a Surose–Maltose Mixture; Killey et al".

Acta Cryst. (1961), 14, pp. 1180–1185; "X–Ray Determination of Crystallinity and Diffuse Disorder Scattering"by W. Ruland.

The Nippon Dental Review, No. 498, pp. 161–171 (1984).

The Japanese Journal of PEDIATRIC DENTISTY, vol. 25, No. 3, pp. 608–613 (1987).

*Primary Examiner*—John W. Rollins
*Assistant Examiner*—Francisco C. Prats
*Attorney, Agent, or Firm*—Browdy and Neimark

[57] ABSTRACT

A novel panose-rich saccharide powder which contains 48–93 w/w % panose, d.s.b., together with other oligosaccharides, and has a crystallinity of 19% or higher on x-ray powder diffraction analysis. The saccharide powder has a substantial non-hygroscopicity, as well as a satisfiable free-flowing ability and stability. Thus, the saccharide powder is advantageously used in food products, cosmetics and pharmaceuticals.

4 Claims, 5 Drawing Sheets

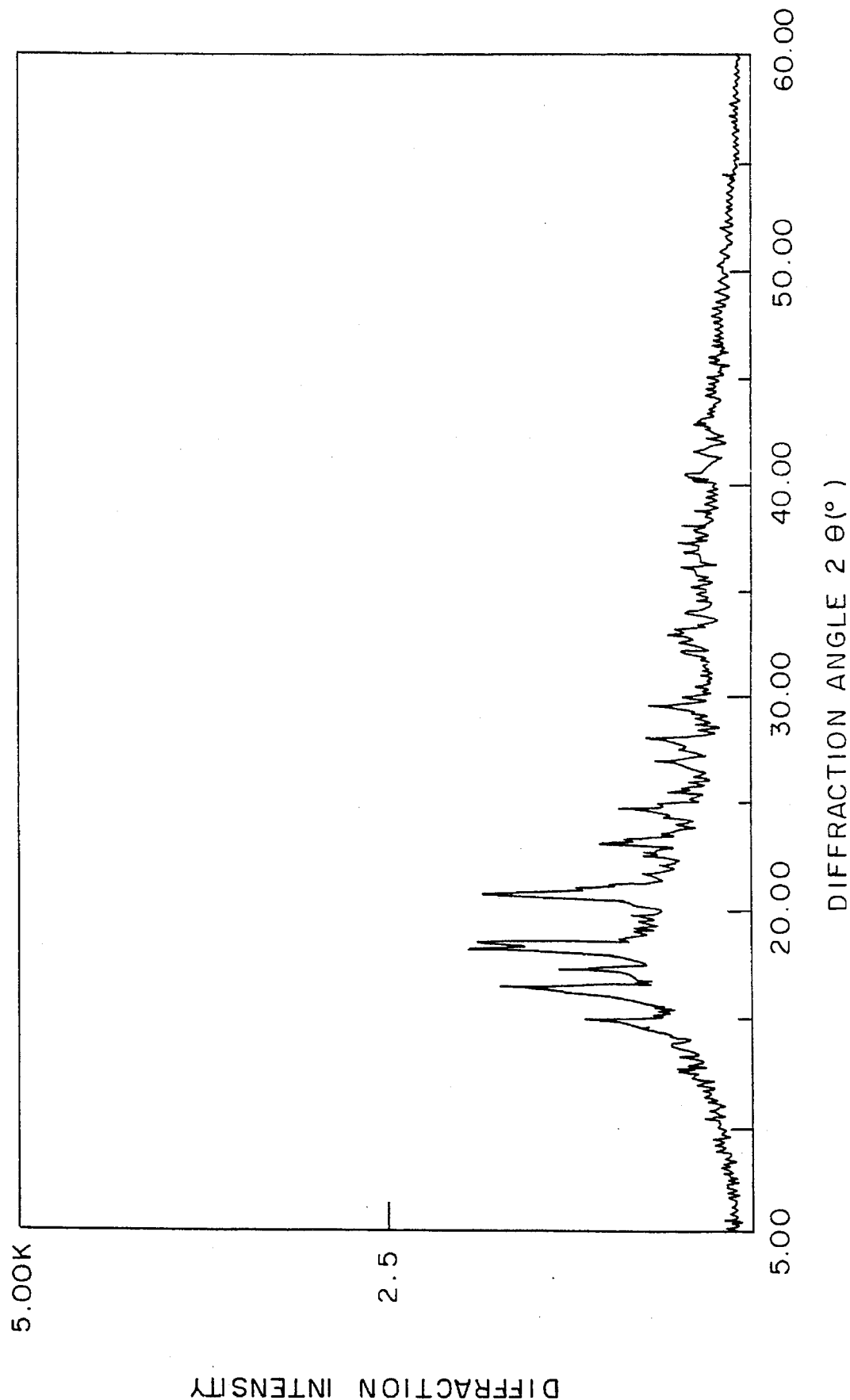

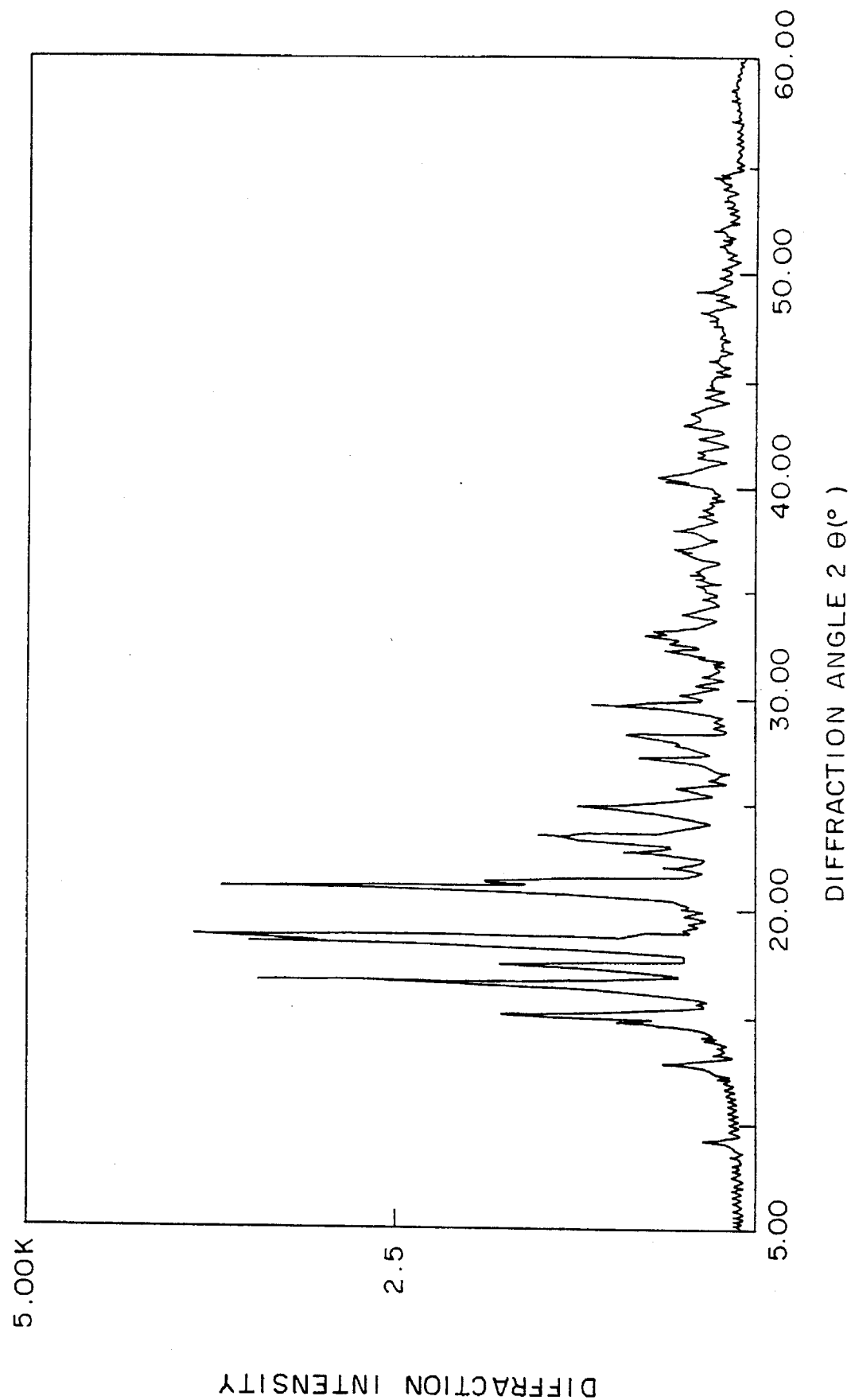

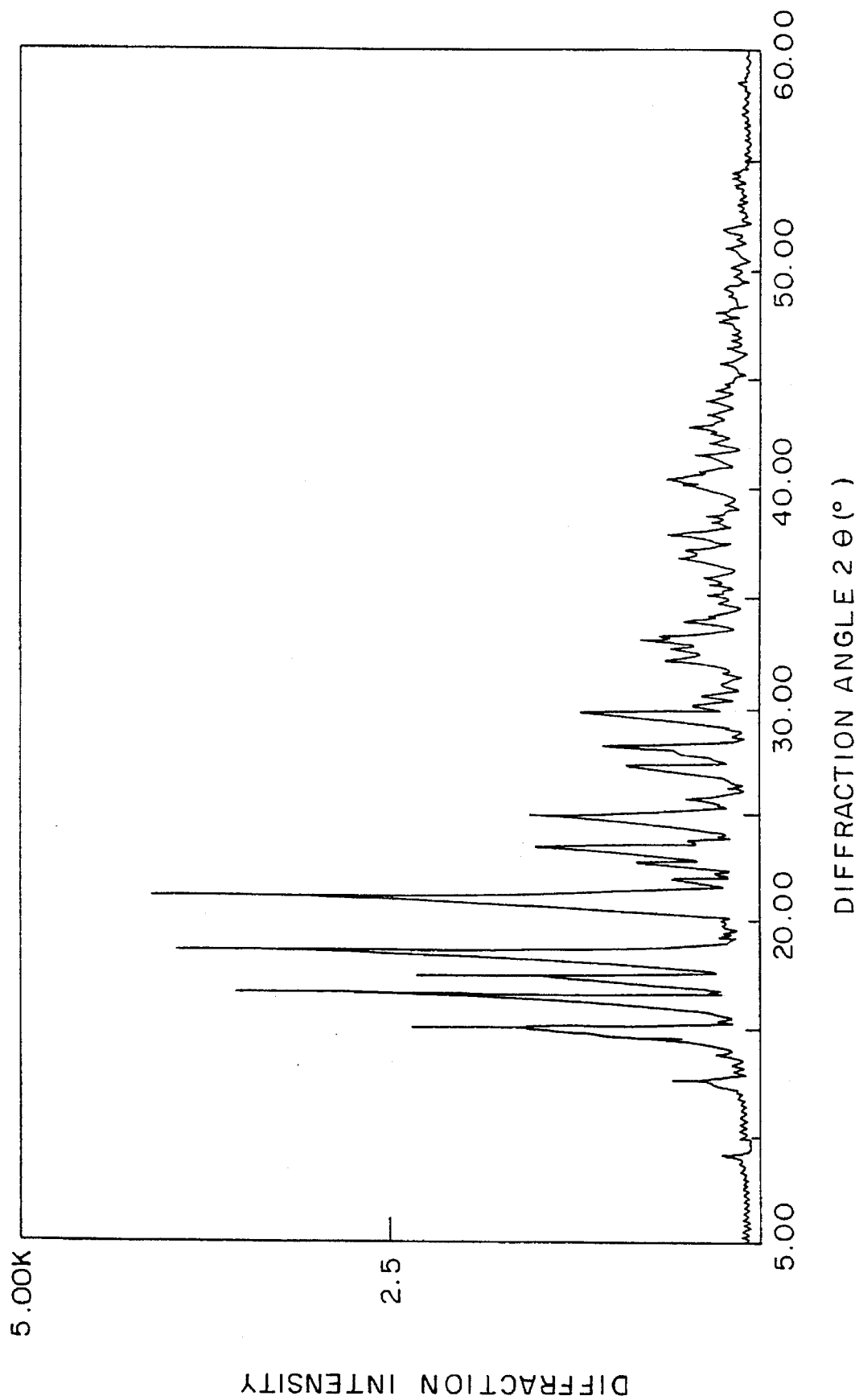

SACCHARIDE IN THE FORM OF POWDER, AND ITS PREPARATION AND USE

This application is a continuation of application Ser. No. 07/894,482, filed Jun. 5, 1992 now abandoned.

BACKGROUND OF THE INVENTION

1. Field of the invention

The present invention relates to a saccharide in the form of powder (abbreviated as "saccharide powder" hereinafter), and its preparation and uses; more particularly, it relates to a saccharide powder, i.e. a panose-rich saccharide containing oligosaccharides together with 48–93% panose (the symbol "%" means "w/w %" throughout the specification as long as no inconvenience occurs), based on the weight of the dry solid (abbreviated as "d.s.b." hereinafter), as well as exhibiting a crystallinity of 19% or higher on x-ray powder diffraction analysis, and its preparation and uses.

2. Description of the Prior Art

As evident from Japanese Patent Publication No. 76,063/83, *The Nippon Dental Review*, No.498, pp.161–171 (Apr., 1984) and *The Japanese Journal of Pediatric Dentistry*, Vol.25, No.3, pp.608–613 (1987), it has been known that (i) dental-caries-inducing microorganisms do not assimilate panose to form water-insoluble glucans, (ii) the formation of water-insoluble glucans from sucrose is strongly reduced when the microorganisms assimilate sucrose in the presence of panose, and (iii) the microorganisms do not assimilate panose to form organic acids, and these render panose advantageously useful as a sweetener having a relatively low- or anti-dental-caries-inducibility, as well as a growth-promoting saccharide for bifid bacteria.

It has been known that a saccharide solution containing panose together with a relatively-large amount of monosaccharides such as glucose and fructose; oligosaccharides such as maltose, isomaltose, maltotriose, isomaltotriose and isomaltosyl maltose; and dextrins is obtained by conventional methods, for example, (1) a process containing a step of subjecting maltose to the action of α-glucosidase (EC 3.2.1.20), (2) a process containing a step of subjecting a mixture of maltose and sucrose to the action of sucrase (EC 2.4.1.5) and (3) a process containing a step of subjecting pullulan or an amylaceous substance to the action of an acid or an enzyme such as α- and β-amylases.

It has been also known that a preparation of a saccharide powder comprising subjecting a saccharide solution prepared by the above conventional preparations to a column chromatography using a strongly-acidic action exchange resin to mainly remove monosaccharides, recoverying a panose-rich fraction with an increased panose-content, concentrating the fraction, and pulverizing the resultant.

The panose-rich saccharide powder thus obtained is, however, usually a mixture of saccharides containing a relatively-large amount of panose and other oligosaccharides.

When the panose-rich saccharide powder is used in food products, the coexistence of oligosaccharides does not hinder the properties of panose as long as the amount of the oligosaccharides dose not reach an excessive level, and improves the yield of the final saccharide product. These may result in an economical benefit and a promotion of an industrial preparation of panose.

It was found that a saccharide powder containing a relatively-large amount of panose together with other oligosaccharides, however, has the following drawback: Since the saccharide has a relatively-high hygroscopicity, it readily solidifies to lose its free-flowing ability. Thus, a relatively-high level of care for the packaging and handling is inevitable.

In the preparation of a panose-rich for providing saccharide powder, there has been a great demand a saccharide powder having a substantial non-hygroscopicity and a satisfactory stability and free-flowing ability by improving the properties of a relatively-high hygroscopic saccharide-powder which contains 7% or higher of oligosaccharides, d.s.b., and has an economical advantage of a relatively-high yield.

SUMMARY OF THE INVENTION

The present inventors have continued studying to obtain a saccharide powder having a substantial non-hygroscopicity and a satisfactory free-flowing ability by improving the properties of conventional panose-rich saccharide powder which contain a relatively-large amount of panose together with 7% or higher of oligosaccharides, d.s.b., and have a relatively-high hygroscopicity.

As a result, the present inventors found that the hygroscopicity of a saccharide powder, which was prepared by adding a seed to a relatively-high concentration solution of a panose-rich saccharide to effect crystallization of panose, was much more reduced than that of a non-crystalline saccharide powder; and that a saccharide powder or a panose-rich saccharide containing oligosaccharides together with 48–93% panose, d.s.b., as well as exhibiting a crystallinity of 19% or higher on x-ray powder diffraction analysis, had a substantial non-hygroscopicity and a satisfactory stability and free-flowing ability. Furthermore, the present inventors established the preparation and uses of the saccharide powder. Thus, the present inventors accomplished this invention.

BRIEF DESCRIPTION OF THE ACCOMPANYING DRAWINGS

FIG. 3 shows an x-ray powder diffraction pattern of a saccharide powder having 48% panose, d.s.b., and a crystallinity of 19% on x-ray powder diffraction analysis.

FIG. 4 shows an x-ray powder diffraction pattern of a saccharide powder having 68% panose, d.s.b., and a crystallinity of 42% on x-ray powder diffraction analysis.

FIG. 5 shows an x-ray powder diffraction pattern of a saccharide powder having 93% panose, d.s.b., and a crystallinity of 60% on x-ray powder diffraction analysis.

DETAILED DESCRIPTION OF THE INVENTION

Figure 1:
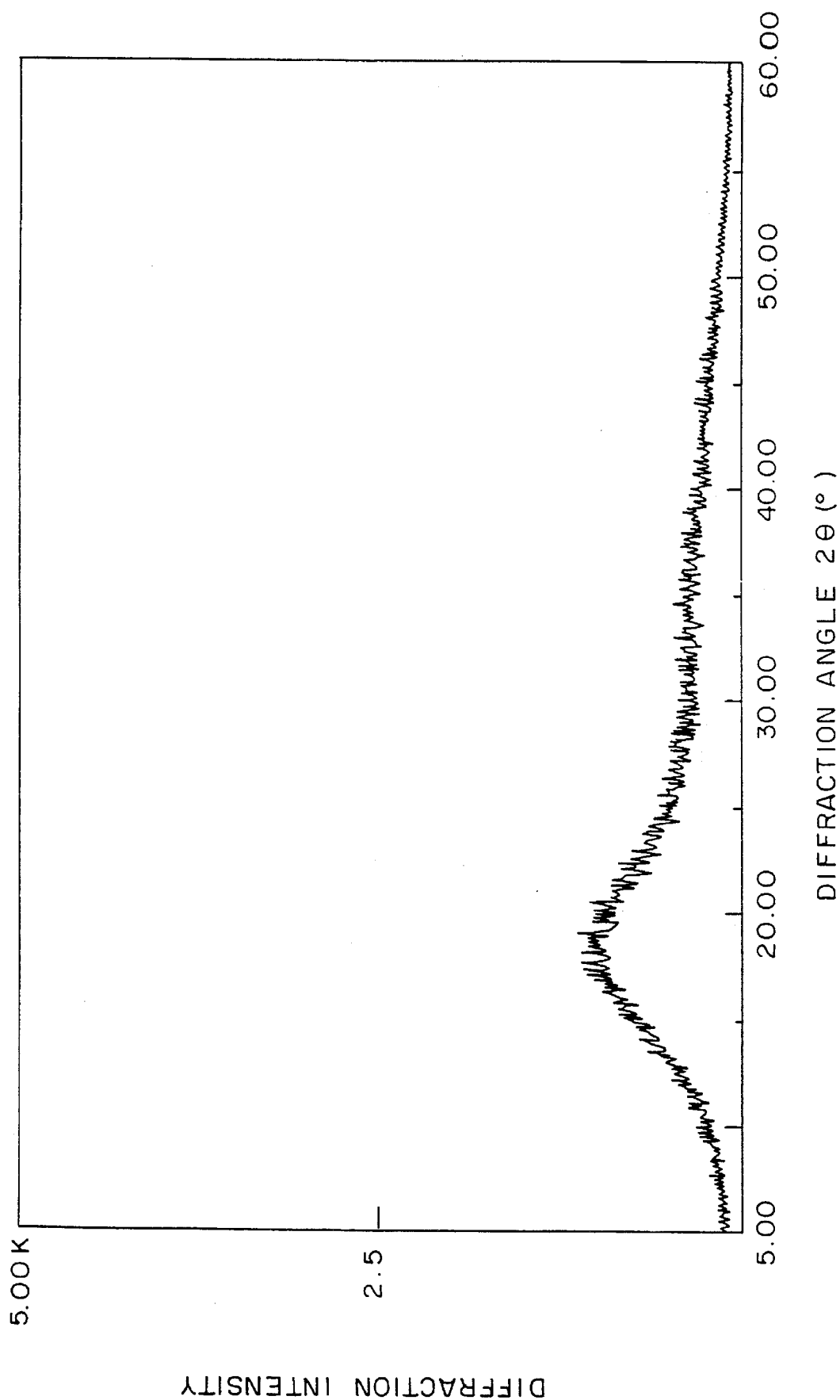
FIG. 1 shows an x-ray powder diffraction pattern of a saccharide powder having 40% panose, d.s.b., and a crystallinity of 0% on x-ray powder diffraction analysis.

The saccharides advantageously usable in the invention are, for example, panose-rich saccharides which contain panose together with 7% or higher of oligosaccharides, said panose-rich saccharides being preparable into a saccharide powder which exhibits a crystallinity of 19% or more on x-ray powder diffraction analysis by crystallizing panose in the saccharides. A suitable saccharide composition of the saccharides is 48–93% panose, d.s.b., preferably, 56–93% panose, d.s.b., and other oligosaccharides.

The processes to prepare such saccharides are adequately chosen from the following representative examples:

(1) *The Nippon Dental Review*, No. 498, pp. 161–162 (April, 1984), *The Japanese Journal of Pediatric Dentistry*, Vol.25, No.3, pp.608–609 (1987) and Japanese Patent Laid-Open Nos. 30,695/85, 219,345/86 and 122,696/88 describe a process for preparing a panose-rich saccharide solution wherein maltose is subjected to the action of α-glucosidase (EC 3.2.1.20), said processes containing a step of either subjecting maltose to the action of α-glucosidase (EC 3.2.1.20) or subjecting a maltose specimen obtained by liquefying and saccharifying starch to the action of α-glucosidase (EC 3.2.1.20) in order to effect saccharide-transferring reaction;

(2) *The Journal of Biological Chemistry*, Vol.200, pp. 793–801 (1953) and *Journal of the American Chemical Society*, Vol. 77, pp.3315 (1955) describe a process for preparing a panose-rich saccharide solution which is prepared by subjecting maltose and sucrose to the action of sucrase, said process containing a step of subjecting a mixture solution of maltose and sucrose to the action of dextransucrase (EC 2.4.1.5) to effect saccharide-transferring reaction; and (3) A process for preparing a panose-rich saccharide solution is described, for example, in Japanese Patent Laid-Open No.760,063/83 wherein pullulan is subjected to the action of an acid or β-amylase (EC 3.2.1.2) to effect partial hydrolysis; and Japanese Patent Laid-Open No.171,493/89 wherein pullulan or starch is subjected to the action of α-amylase (EC 3.2.1.1 or neopullulanase) to effect partial hydrolysis.

The panose content in the saccharide solutions thus obtained is usually in the range of about 10–70%, d.s.b. If the panose content is required to increase, the saccharide solutions can be adequately subjected to a gel chromatography, membrane separation and/or column chromatography using an activated charcoal.

A column chromatography using a strongly-acidic cation exchange resin described in Japanese Patent Laid-Open Nos.148,794/84 and 30,695/85, as well as in *The Nippon Dental Review*, No.498, page 162 (Apr., 1984), can be advantageously employed to obtain a psnose-rich saccharide.

The panose-rich saccharides containing oligosaccharides together with 48–93% panose, d.s.b., usable in the invention can be prepared by one of the processes described above or by combining two or more of them.

The processes usable in the present invention are those which can prepare a saccharide powder having a substantial non-hygroscopicity, i.e. processes comprising crystallizing panose in a relatively-high concentration solution of a panose-rich saccharide, and pulverizing the resultant mixture to obtain the saccharide powder. For example, a process comprising either placing a relatively-high concentration solution of a panose-rich saccharide, or, preferably placing an aqueous panose solution having a concentration of 70–95% in a container such as a crystallizer, adding thereto an adequate amount of panose as a seed, preferably, 0.01–2% of panose, d.s.b, mixing the resultant to effect crystallization of panose and to form a massecuite, pulverizing the resultant, and recovering the resultant powder.

It was found that the powder should be prepared into a saccharide powder having a crystallinity of 19% or higher, preferably, 30% or higher, on x-ray powder diffraction analysis in order to impart to the powder a substantial non-hygroscopicity and a satisfactory stability and free-flowing ability.

In the present invention, it is preferable to prepare from a massecuite a saccharide powder having the highest possible level of crystallinity by adequately combining conventional pulverization methods such as spray-drying, fluidized-bed granulation and block pulverization.

In the spray-drying, a substantially non-hygroscopic saccharide powder can be obtained by spraying from a nozzle a massecuite having a concentration of 70–85% and 5–30% crystalline panose, d.s.b, with a high-pressure pump, and drying the resultant with a hot-air such as 60°–100° C. air which dose not melt a saccharide powder having a crystal. The resultant mixture is subjected to effect crystallization and ageing by blowing thereto a 30°–60° C. air for about 1–24 hours to give a crystallinity of 19% or higher.

In the block-pulverization, a substantially non-hygroscopic saccharide powder can be usually obtained by allowing to stand for about 1–10 days a massecuite having a concentration of 85–95% and about 1–30% crystalline panose, d.s.b., to effect crystallization, solidifying the whole content into a block, pulverizing the resultant block with a pulverizer or a cutter, and drying the resultant powder to give a crystallinity of 19% or higher.

Furthermore, a substantial non-hygroscopic saccharide powder can be advantageously prepared in an usual manner by concentrating a relatively-high concentration solution of a panose-rich saccharide under heating conditions to give a moisture content of below 5%, kneading the resultant super-saturated solution of a panose-rich saccharide in a melt-like condition with a seed under the melting point, pulverizing the resultant mixture by the methods such as fluidized-bed granultaion or extruding granulation into a powder having an appropriate form such as granules and fine- and coarse-powders, followed by crystallizing and ageing the powder to give a crystallinity of 19% or higher.

Although the properties of the present panose-rich saccharide powder thus obtained are dependently changed on the panose content and the degree of crystallinity, the saccharide powder having a crystallinity of 19% or higher is substantially non-hygroscopic, free from solidification, satisfactorily stable and readily handleable, and these properties reduce by a large margin the material- and labor-costs required in the care of packaging, transportation and storage.

The present saccharide powder is substantially non-hygroscopic, and this advantageously facilitates the preparations of products such as a mixed sweetener in powder, chocolate, chewing gum, powdered juice, instant soup, granules and tablet which have been deemed very difficult to prepare with conventional panose-rich powders.

The present saccharide powder, similarly as conventional panose in the form of aqueous solution or non-crystalline powder, has properties of panose per se such as sweetening power, energy-imparting ability, body-imparting ability, gloss-imparting ability, moisture-retaining ability, crystallization-preventing ability for other saccharides, viscosity, thermal stability, acid tolerance, substantial non-fermentability, and relatively low- and anti-dental-carries-inducibility, and these render the present saccharide powder advantageously useful in the variety of fields such as food products, cosmetics and pharmaceuticals.

The present saccharide powder can be used as a sweetener in combination with an adequate amount of other one or more sweeteners, for example, starch sugar powder, glucose, maltose, isomerized sugar, sucrose, honey, maple sugar, sorbitol, dihydrochalcone, stevioside, α-glycosyl stevioside, sweenener of Fructus Momordicae, glycyrrhizin, L-aspartyl L-phenylalanine methyl ester, saccharin, glycine and alanine. The saccharide powder can be mixed with a filler such as dextrin, starch and lactose, prior to use.

The saccharide powder can be molded solely or after mixing it with filler, vehicle and/or binder into a granule, sphere, tablet, rod, sheet or cubic, prior to use.

Since the saccharide powder is substantially not assimilated by dental-carries-inducing microorganisms, it can be used as a sweetener having an anti-dental-carries-inducibility. The saccharide powder can be suitably used as a sweetener in food products having a relatively-low dental-carries-inducibility, for example, confectioneries such as chewing gum, chocolate, biscuite, cookies, caramel and candy; and soft drinks such as cola, carbonated drink, juice, coffee and lactic acid beverage. , The saccharide powder can be favorably used as a sweetener in cosmetics, pharmaceuticals and products to prevent dental carries such as a gargle and dentifrice.

The saccharide powder can be advantageously used not only in the aforesaid products but also in foods and beverages in general to impart to them a sweetness, as well as to improve their tastes and qualities, because the saccharide powder has a relatively-high tolerance to acid and heat, as well as having a sweetness which well harmonizes with other sour-, salty-, bitter-, delicious- and astringent-substances.

Thus, the saccharide powder can be advantageously used in foods and beverages in general, for example, seasonings such as soy sauce, say sauce powder, miso, miso powder, "moromi", "hishio", "furikake", mayonnaise, dressing vinegar, "sanbai-zu", "funmatsu-sushi-su", "chuka-no-moto", "tentsuyu" (soup for tenpura), "mentsuyu" ( soup for Japanese-style noodles ), Worcester sauce, ketchup, "yakiniku-no-tare" (soup for grilled meat), curry roux, stew premix, soup premix, "dashi-no-moto", mixed seasoning, "mirin" (heavily sweetened sake), "shin-mirin" (synthetic mirin), table sugar and coffee sugar.

The saccharide powder can be advantageously used in foods and beverages in general to impart to them a sweetness and to improve their tastes and qualities. Examples of such foods and beverages are Japanese-style confectioneries such as "senbei" (rice crackers), "arare" (pellet-shaped senbei), "okoshi" (millet and rice cracker) , rice paste, "manju" (bun with a bean-jam filling), "uiro" (sweet rice jelly), "an" (bean jam) , "yokan" (sweet jelly of beans) , "mizu-yokan" (soft adzuki-bean jelly), "kingyoku", jelly, castella and "amed-ama" (Japanese-style toffee); Western-style confectioneries such as bun, biscuit, cracker, cookie, pie, pudding, butter cream, custard cream, cream puff, waffle, sponge cake, doughnut, chocolate, chewing gum, caramel and candy; frozen desserts such as ice cream and sherbet; syrups such as those for fruit preserve and "kaki-gori" (shaved ice); pastes such as flour paste, peanut paste and fruit paste; processed fruits such as jam, marmalade, syrup-preserved fruit and crystallized fruit; processed foods of vegetables; processed foods of grain such as breads, noodles, rice products and artificial meats; pickled products such as "fukujin-zuke" (sliced vegetables picked in soy sauce), "bettara-zuke" (fresh radish pickles), "senmai-zuke" and "rakkyo-zuke" (pickled shallots); premixes for pickled products such as "takuan-zuke-no-moto" and "hakusai-zuke-no-moto"; meat products such as ham and sausage; fish meat products such as fish meat ham, fish meat sausage, "kamaboko" (boiled fish paste), "chikuwa" (literally bamboo wheels) and "tenpura" ( deep-fried foods ); relishes such as "uni-no-shiokara" (salted guts of sea urchin), "ika-no-shiokara" (salted guts of squid), "su-konbu", "saki-surume" and "fugu-no-mirinboshi"; "tsukudani" (food boiled down in soy sauce) such as those of "nori" (dried seaweed), "sansai" (mountain vegetables), "surume" (dried squid), small fish and shellfish; daily dishes such as "nimame" (cooked beans), potato salad and "konbu-maki" (tangle roll); milk products; bottled and canned products such as those of meat, fish meat, fruit and vegetable; alcoholic products such as "sake" (fermented rice wine), "mirin" (sweetened sake) and synthetic sake, liqueur, wine and whisky; beverages such as coffee, cocoa, juice, carbonated beverage, lactic acid beverage and lactobacillus beverage; premixes and instant foodstuffs such as pudding premix, hot cake premix, powdered juice, instant coffee, "sokuseki-shiruko" (premix of adzuki—bean soup with rice cake) and instant soup; and agents such as taste-improving agents and quality-improving agents.

The saccharide powder can be advantageously used in feeds and pet foods for domestic animals and poultries including honey bee, silkworm and pet fish for the improvement of the taste qualities of the feeds and pet foods. The saccharide powder can be advantageously used as a sweetener, taste-improving agent and quality-improving agent in special foods and beverages, cosmetics and pharmaceuticals, for example, cigar, cigarette, dentifrice, lipstick, lip cream, internal medicine, troche, cod-liver oil drop, oral refreshing agent, cachou and gargle in the form of a solid, paste or liquid.

In addition, the saccharide powder can be advantageously mixed with vitamins, antibiotics and/or lactic acid bacteria and formed into variety of shapes such as granule and tablet with a granulator and tabletting machine, respectively. The products thus obtained can be used in variety of fields.

Any method to incorporate the saccharide powder in orally-administrable products such as foods, beverages, cigarette, tabacco, feeds, pet foods, cosmetics and pharmaceuticals can be used in the invention, as long as the saccharide powder can be incorporated in the products thereby before completion of their processing. For example, conventional methods such as mixing, kneading, dissolving, melting, soaking, permeating, spreading, applying, coating, spraying, injecting, crystallizing and solidifying are freely chosen.

The present invention will be explained by the following Experiments.

Experiment 1

Preparation of panose-rich saccharide solution

Experiment 1—1

Preparation of panose-rich saccharide solution by using α-glucosidase

"SUNMALT®", a maltose powder commercialized by Hayashibara Co., Ltd., Okayama, Japan, was prepared into a 30% aqueous solution which was then added against maltose, d.s.b., with 0.08% "Transglucosidase L Amano", an enzyme preparation containing α-glucosidase commercialized by Amano Pharmaceutical Co., Ltd., Nagoya, Japan, adjusted to pH 5.5, allowed to react at 55° C. for 18 hours, and heated to inactivate the remaining enzyme.

The resultant solution was in an usual manner purified by filtration, decoloration and deionization using an ion-exchange resin ($H^+$—and $OH^-$—forms) and concentrated into about 50% panose-rich saccharide solution.

The sugar composition of the saccharide solution thus obtained was 21.4% glucose, 17.6% maltose, 9.9% isomaltose, 4.3% maltotriose, 29.8% panose, 1.7% isomaltotriose and 15.3% tetrasaccharides and higher molecular weight of saccharides, d.s.b.

Experiment 1–2

Preparation of panose-rich saccharide solution by using dextransucrase

Experiment 1–2 (A)

Preparation of dextransucrase

Twenty liters of a culture medium consisting of 4 w/v % sugar, 0.5 w/v % yeast extract, 0.8 w/v % potassium dihydrogenphosphate, 2.4 w/v % dipotassium hydrogenphosphate, 0.02 w/v % magnecium sulfate heptahydrate and 0.002 w/v % managanese sulfate was inoculated with one v/v % seed culture of *Leuconostoc mesenteroides* ATCC 10830a, and subjected to a stationary culture at 25° C. for 24 hours.

The resultant culture medium was centrifuged to obtain a supernatant which was then concentrated until the volume was lowered to 2L by using "AIL-1010", a UF-membrane (cut-off 6,000) commercialized by Asahi Chemical Industry, Co., Ltd., Tokyo, Japan. Thus, a crude enzyme solution was obtained.

The activity of dextransucrase was determined with the reducing power of fructose which was formed by adding 2 ml solution of a dextransucrase specimen to 2 ml of 20 w/v % sucrose solution (pH 5.5), and incubating the mixture at 30° C. for 30 minutes.

One unit activity of the dextransucrase was defined as the amount of enzyme that releases 0.25mg fructose from sucrose per 30 minutes.

Experiment 1–2 (B)

Preparation of panose-rich saccharide solution

A mixture of 8 parts by weight of "SUNMALT®", a maltose powder commercialized by Hayashibara Co., Ltd., Okayama, Japan, and 2 parts by weight of sucrose was prepared into a 30% aqueous solution which was then adjusted to pH 5.5, heated to 30° C., added with 100 units per g sucrose of a crude enzyme solution of dextransucrase which had been prepared by the method in Experiment 1–2(A), and subjected to an enzymatic reaction for 24 hours while keeping the pH and temperature. Thereafter, the solution was heated to inactivate the remaining enzyme.

The resultant solution was in an usual manner purified and concentrated to obtain about 50% panose-rich saccharide solution. The sugar composition of the panose-rich saccharide solution was 8.0% fructose, 0.5% glucose, 62.4% maltose, 0.5% isomaltose, 25.0% panose and 3.6% tetraoligo-saccharide and higher molecular weight of saccharides, d.s.b.

Experiment 1–3

Preparation of panose-rich saccharide solution

Panose-rich saccharide solutions of Experiments 1—1 and 1–2 were used in this Experiment as a material. "Amberlite XT-1007 (Na⁺—form, polymerization degree of 6%)", a strongly-acidic action exchange resin commercialized by Tokyo Chemical Company, Tokyo, Japan, was used as a resin for fractionation. The resin was packed in jacketted stainless-steel columns having an inner diameter of 5.4 cm and 2 columns of which were cascaded to flow a saccharide solution in series and to give a total gel-bed depth of 10 m.

Five v/v % of a saccharide-solution as a material was first added against the resin while keeping the inner temperature of the columns at 55° C., then 55° C. water was fed to the columns at a flow rate of SV 0.5 to effect fractionation, followed by recoverying a panose-rich saccharide fraction containing a relatively-large amount of panose together with other oligosaccharides. The panose-rich saccharide fraction was in an usual manner purified and concentrated into a panose-rich saccharide solution in the form of syrup.

In the above fractionation, a panose-rich saccharide solution containing 40%, 45%, 48% or 68% panose, d.s.b., was obtained from a panose-rich saccharide solution prepared by the method in Experiment 1—1, while a panose-rich saccharide solution containing 56%, 79% or 93% panose, d.s.b., was obtained from a panose-rich saccharide solution prepared by the method in Experiment 1–2.

Experiment 2

Effect of panose content and crystallinity of saccharide powder on its physical properties Panose-rich saccharide solutions prepared by the methods in Experiments 1—1, 1–2 and 1–3 were respectively concentrated into about 88% solutions which were then placed into small crystallizers, added with 0.1% panose, d.s.b., as a seed, mixed to effect crystallization, transferred to polyethylene vessels, and allowed to stand at 37° C. for 7 days. Thereafter, the resultants were dried and pulverized to obtain saccharide powders having a moisture content of below 2%.

The crystallinity of the saccharide powders was determined by the Ruland method based on a pattern of x-ray powder diffraction analysis, reported in *Acta Crystallographica*, Vol.14, pp.1180–1185 (1961), wherein "GEIGERFLEX RAD-II B (CuK$\alpha$ ray)", an apparatus for x-ray diffraction analysis produced by Rigaku Co., Tokyo, Japan, was used an x-ray diffraction apparatus.

The representative x-ray powder diffraction patterns of the saccharide powders were as shown in FIGS. 1–5. It was found that the crystalline saccharide powders as shown in FIGS. 2–5 exhibited the peaks of predominant diffraction angles (2$\Theta$) of 16.4°, 18.2°, 18.5° and 20.8°.

These saccharide powders were placed in aluminum containers and allowed to stand at a relative humidity of 75.2% and a temperature of 25° C. for 3 days. Thereafter, the degree of hygroscopicity (weight increase), satisfiability of freeflowing ability and the presence of solidification were observed.

In order to quantitatively determine the level of the free-flowing ability of the saccharide powders, the angle of repose or poured angle of repose was measured.

The method to measure the angle of repose was as follows: Keep the outlet edge of a funnel made of polyethylene at a height of 80 mm, said funnel having a cylindrical part with 110 mm in diameter and 20 mm in height, a cone part with 100 mm in height, and an outlet with 10 mm in diameter; fill up a saccharide powder in the funnel; freely drop the saccharide powder from the outlet of the funnel; and measure the angle of the falling substances.

The results were as shown in Table.

TABLE

Figure 2:
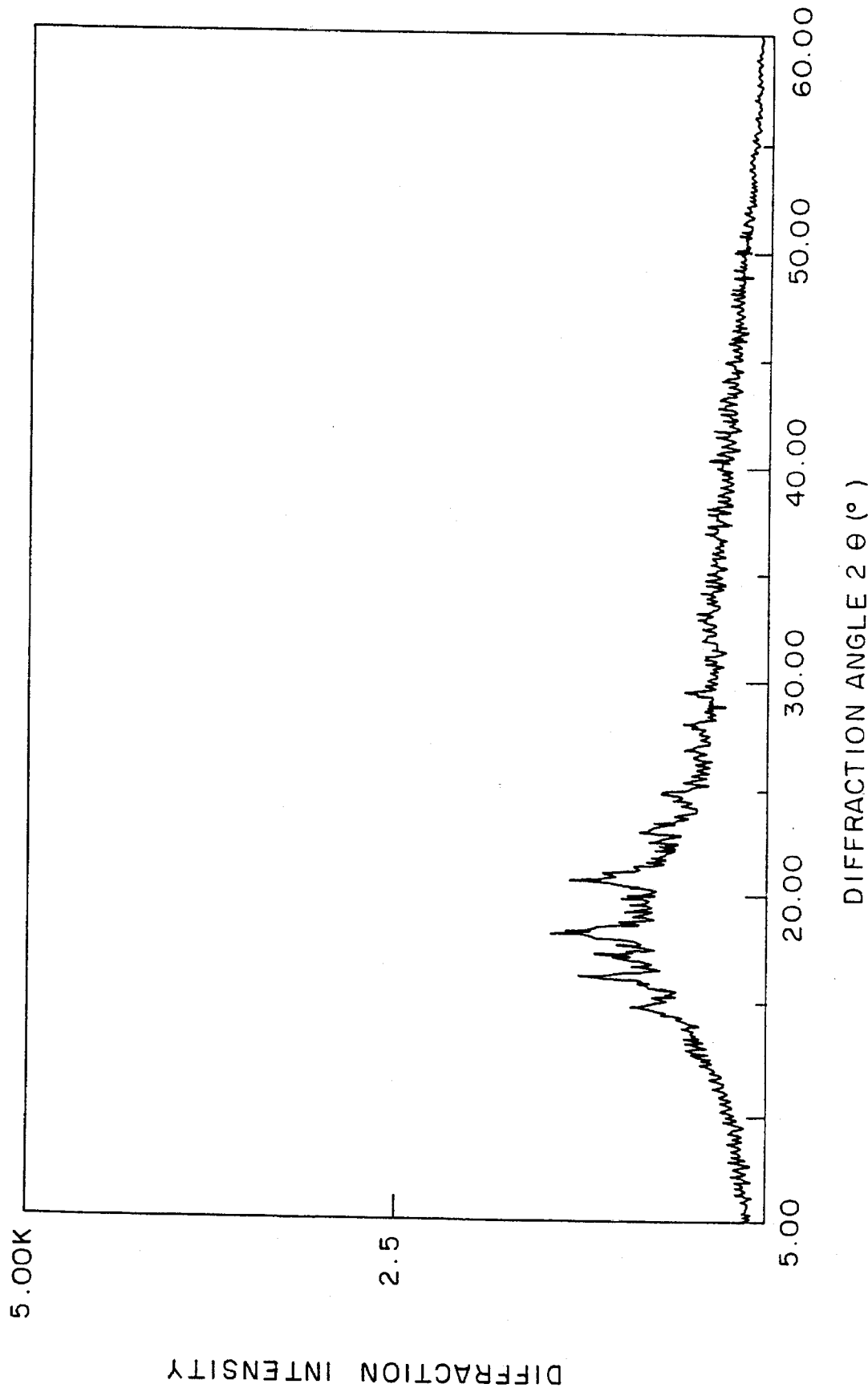
FIG. 2 shows an x-ray powder diffraction pattern of a saccharide powder having 45% panose, d.s.b., and a crystallinity of 11% on x-ray powder diffraction analysis.

| Content of panose (%) | Cystallinity (%) | Powdery x-ray diffraction pattern | Increase of weight (%) | Free-flowing ability | Solidification | Angle of repose (Poured angle of repose) (°) | Judgement |
|---|---|---|---|---|---|---|---|
| 25 | 0 |  | 15.5 | Unsatisfactory | Present | Indeterminable | Control |
| 30 | 0 |  | 15.2 | Unsatisfactory | Present | Indeterminable | Control |
| 40 | 0 | FIG. 1 | 15.0 | Unsatisfactory | Present | Indeterminable | Control |
| 45 | 11 | FIG. 2 | 7.6 | Unsatisfactory | Present | Difficult | Control |
| 48 | 19 | FIG. 3 | 2.4 | Satisfactory | Not present | 42 | Present invention |
| 56 | 30 |  | 1.4 | Satisfactory | Not present | 40 | Present invention |
| 68 | 42 | FIG. 4 | 1.1 | Satisfactory | Not present | 39 | Present invention |
| 79 | 50 |  | 0.9 | Satisfactory | Not present | 38 | Present invention |
| 93 | 61 | FIG. 5 | 0.7 | Satisfactory | Not present | 36 | Present invention |

As evident from the results in Table, saccharide powders having a panose content of 40% or lower, d.s.b., do not crystallize psnose and those having 45% panose, d.s.b., crystallize panose as shown in FIG. 2. However, the crystallinity of the latter is low as 11%. Improvement of the properties of such saccharide powders can hardly be expected.

It was found that saccharide powders as shown in FIGS. 3–5 having a panose content in the range of 48–93%, d.s.b., and a crystallinity of 19% or higher, are satisfactory saccharide powders having a strongly-reduced hygroscopicity, as well as a satisfactory stability and free-flowing ability.

As a control, saccharide solutions containing 25–93% panose, d.s.b., were concentrated and spray-dried into non-crystalline saccharide powders having a moisture content of below 2%, which were then allowed to stand at the same conditions as above for 3 days. Every saccharide powder exhibited a relatively-strong hygroscopicity to lose its free-flowing ability, followed by solidification.

Experiment 3

Test on long-term storage

Two hundred and fifty g aliquots of panose-rich saccharide powders prepared by the method in Experiment 2 were placed in polyethylene bags, and subjected to a one-year storage test under room conditions, i.e. a relative humidity of about 40–90% and a temperature of about 5°–30° C. As a result, every saccharide powder having a panose content of below 45%, d.s.b., and a crystallinity of below 11% was solidified to lose its free-flowing ability.

While saccharide powders having a panose content of 48–93%, d.s.b., and a crystallinity of 19% or higher had a satisfactory stability.

More particularly, a saccharide powder having the minimum panose content of 48%, d.s.b., and the minimum crystallinity of 19% showed a slight solidification, but the resultant semi-solid product was readily disintegrated into a powder by a slight shock.

It was found that a saccharide powder having a panose content of 56% or higher, d.s.b., and a crystallinity of 30% or higher was extremely stable without solidification.

Preferred examples of the present invention will be described hereinafter.

Examples A and B will illustrate the preparations and uses of the present saccharide powder.

Example A-1

Saccharide powder

"HM-75", a maltose syrup commercialized by Hayashibara Co. Ltd., Okayama, Japan, was diluted with water into a 35% aqueous solution which was then added with 0.05% per maltose, d.s.b., of a crude enzyme preparation containing α-glucosidase prepared by the method in Experiment 1—1, and the mixture was adjusted to pH 5.5, heated to 55° C., and subjected to an enzymatic reaction for 14 hours. Thereafter, the resultant mixture was heated to inactivate the remaining enzyme to obtain a saccharide solution containing panose.

The solution thus obtained was in an usual manner purified and concentrated into a solution having a concentration of about 60%, and the resultant solution was subjected to a column chromatography using a strongly-acidic cation exchange resin in accordance with the method in Experiment 1–3 to obtain a panose-rich saccharide fraction.

"DOWEX 50WX4 ($Na^+$—form)", a strongly-acidic cation exchange resin commercialized by Dow Chemical Company, Midland, Mich., USA was used as a resin for fractionation.

A column packed with the resin was added with 5 v/v % of a saccharide solution against the resin while keeping the inner temperature of the column at 75° C., and fed with 75° C. hot-water at a flow rate of SV 0.4 to effect fractionation, followed by recoverying a panose-rich fraction containing about 56% panose, d.s.b. The fraction was in an usual manner purified by decoloration and deionization, and concentrated in vacuo to give a concentration of about 90%. The resultant solution was transferred to a crystallizer, added with about one % seed, d.s.b., mixed to effect crystallization, transferred to a plastic vessel, and allowed to stand at 35° C. for 5 days. Thereafter, the resultant mixture was pulverized by a pulverizer and dried to obtain a saccharide powder in the yield of 40%.

The product containing about 56% panose, d.s.b., together with other saccharides such as maltose, isomaltose, maltotriose, isomaltotriose, and a small amount of tetraoligosaccharide or higher molecular weight of saccharides exhibited a crystallinity of 30% on x-ray powder diffraction analysis.

The product was a saccharide powder having a substantial non-hygroscopicity and a satisfactory stability and free-flowing ability.

The product has a moderate sweetness and a relatively-low dental-carries-inducibility, and these render the product advantageously useful as a sweetener in tastable foods and beverages.

Example A-2

Saccharide powder

"MALTOSE H", a maltose powder commercialized by Hayashibara Biochemical Laboratories Inc., Okayama, Japan, was prepared into a 40% aqueous solution which was then similarly as in Example A-1 subjected to the action of a crude enzyme preparation containing α-glucosidase to obtain a panose-rich saccharide solution. The resultant solution was subjected to a column chromatography using a strongly-acidic cation exchange resin to obtain a panose-rich fraction containing 80% panose, d.s.b., which was then purified, concentrated to give a concentration of about 82%, transferred to a crystallizer, added with about one %, seed, d.s.b., mixed to effect crystallization, and gradually cooled from 55° C. under a gentle stirring-condition to obtain a massecuite having about 20% crystalline panose, d.s.b.

The massecuite was sprayed at a pressure of 150 kg/cm$^2$ by a high-pressure pump from a nozzle, 1.5 mm in diameter, equipped at the top of a spraying tower.

Simultaneously, 90° C. hot-air was blown to the content from the top of the spraying tower, and the resultant saccharide powder was recovered on a wire-net conveyer equipped on the base of the spraying tower. The saccharide powder on the conveyer was gradually conveyed from the spraying tower while flowing thereto 50° C. hot-air from under the conveyer for about 40 minutes. The saccharide powder thus obtained was injected into an ageing tower, crystallized and aged for 15 hours to complete the crystallization and drying, followed by recoverying a saccharide powder in the yield of about 20%.

The product had about 80% panose, d.s.b., together with other oligosaccharides such as maltose, isomaltose, maltotriose and isomaltotriose, and exhibited a crystallinity of about 51% on x-ray powder diffraction analysis.

The product was a saccharide powder having a substantial non-hygroscopicity and a satisfactory stability and free-flowing ability.

Similarly as the product in Example A-1, the product has a moderate sweetness and a relatively-low dental-carries-inducibility, and these render the product advantageously useful as a sweetener in tastable foods and beverages.

Example A-3

A suspension containing 2 parts by weight of corn starch and 7 parts by weight of water was added with a commercially-available liquefying α-amylase derived from a microorganism, and heated to 90°–100° C. to effect gelatinization and liquefaction. Thereafter, the mixture was heated at 130° C. to cease the enzymatic reaction, followed by recoverying a liquefied solution with a dextrose equivalent (DE) of about 2. The resultant solution was first cooled to 55° C., then added with 150 units per g starch of isoamylase (EC 3.2.1.68) derived from a microorganism of the species *Pseudomonas amyloderamosa* commercialized by Hayashibara Biochemical Laboratories Inc., Okayama, Japan, and 40 units per g dextrin of β-amylase (EC 3.2.1.2) commercialized by Nagase Biochemicals Ltd., Kyoto, Japan. The resultant mixture was kept at pH 5.0 and subjected to an enzymatic reaction for 24 hours to obtain a maltose-rich saccharide solution which was then heated to inactivate the remaining enzyme. Thus, a maltose-rich saccharide solution was obtained.

In accordance with the method in Experiment 1—1, the maltose-rich saccharide solution was subjected to the action of a crude preparation containing α-glucosidase to obtain a saccharide solution containing panose. In accordance with the method in Experiment 1–3, the resultant saccharide solution was subjected to a column chromatography using a strongly-acidic action exchange resin to obtain a panose-rich saccharide solution having about 70% panose, d.s.b., which was then purified, concentrated to give a concentration of about 88%, and, similarly as in Example A-1, crystallized and pulverized to obtain a saccharide powder in the yield of about 30%.

The product contained about 70% panose, d.s.b., together with other glucooligosaccharides such as maltose, isomaltose, maltotriose and isomaltotriose, as well as a small amount of higher molecular weight of saccharides, and exhibited a crystallinity of 43% on x-ray powder diffraction analysis.

The product was a saccharide powder having a substantial non-hygroscopicity and a satisfiable stability and free-flowing ability.

Similarly as the product in Example A-1, the product has a moderate sweetness and a relatively-low dental-carries-inducibility, and these render the product advantageously useful as a sweetener in tastable foods and beverages.

Example A-4

A mixture containing 3 parts by weight of sucrose and 7 parts by weight of "SUNMALT-S®", a maltose powder commercialized by Hayashibara Co., Ltd., Okayama, Japan, was prepared into a 30% aqueous solution. In accordance with the method in Experiment 1–2, the resultant aqueous solution was subjected to the action of dextransucrase to obtain a panose-rich saccharide solution.

In accordance with the method in Example A-1, the resultant saccharide solution was subjected to a column chromatography using a strongly-acidic action exchange resin to obtain a panose-rich saccharide fraction having about 92% panose, d.s.b. In accordance with the method in Example A-2, the resultant panose-rich fraction was purified, concentrated and crystallized to obtain a massecuite which was then spray-dried to obtain a saccharide powder in the yield of about 13%.

The product contained about 92% panose, d.s.b., together with other oligosaccharides such as maltose, isomaltose and isomaltotriose, as well as higher molecular weight of saccharides, and exhibited a crystallinity of 60% on x-ray powder diffraction analysis.

The product was a saccharide powder having a substantial non-hygroscopicity and a satisfactory stability and free-flowing ability.

Similarly as the product in Example A-1, the product has a moderate sweetness and a relatively-low dental-carries-inducibility, and these render the product advantageously useful as a sweetener in tastable foods and beverages.

Example A-5

A pullulan specimen was dissolved in 0.66N aqueous hydrochloric acid solution to give a concentration of 10 w/v %, and the resultant solution was kept at 95° C. for 30 minutes, cooled to 40° C., adjusted to pH 4.5 by the addition of aqueous sodium hydroxide solution, added with 29 units per g pullulan of glucoamylase (EC 3.2.1.3) commercialized by Nagase Biochemicals Ltd., Kyoto, Japan, while keeping the pH and temperature, and heated to inactivate the remaining enzyme. Thus, a panose-rich saccharide solution was obtained.

In accordance with the method in Example A-1, the resultant panose-rich saccharide solution was fractionated by a column chromatography using a strongly-acidic action exchange resin to obtain a panose-rich fraction having about 77% panose, d.s.b., which was then purified and concentrated to give a concentration of about 90%. Thereafter, the resultant solution was similarly as in Example A-1 crystallized and pulverized to obtain a saccharide powder in the yield of about 5%.

The product contained about 77% panose, d.s.b., together with other glucooligosaccharides such as maltose, isomaltose and isomaltosylmaltose, as well as a small amount of higher molecular weight of saccharides, and exhibited a crystallinity of 47% on x-ray powder diffraction analysis.

The product was a saccharide powder having a substantial non-hygroscopicity and a satisfactory stability and free-flowing ability.

Similarly as the product in Example A-1, the product has a moderate sweeteness and a relatively-low dental-carries-inducibility, and these render the product advantageously useful as a sweetener in tastable foods and beverages.

Example B-1

Mixed sweetener

Six parts by weight of sucrose and 4 parts by weight of a panose-rich saccharide powder prepared by the method in Example A-3 were mixed to homogeneity to obtain a mixed sweetener.

The product is a sweetener having a satisfactory sweetness and a relatively-low dental-carries-inducibility.

Example B-2

Mixed sweetener

To 800 parts by weight of crystalline maltitol was mixed to homogeneity 195 parts by weight of panose-rich saccharide powder prepared by the method in Example A-5, 5 parts by weight of "αG sweet", an α-glycosyl stevioside commercialized by Toyo Sugar Refining Co., Ltd, Tokyo, Japan, and the resultant mixture was sprayed with a small amount of water and pressed with a relatively-low level of pressure to obtain a mixed sweetener in the form of cubic.

The product is a sweetener having the same level of sweetening powder of sucrose, as well as having a relatively-high quality sweetness and a relatively-low dental-carries-inducibility.

Example B-3

Cream wafers

Two thousand parts by weight of a saccharide powder prepared by the method in Example A-1, 1,000 parts by weight of shortening, one part by weight of lecithin, one part by weight of lemon oil, and an adequate amount of vanilla oil were mixed in an usual manner, and the resultant cream was kept at 40°–45° C. while heating, and sandwiched between wafers to obtain cream wafers.

The product has a satisfactory taste and a relatively-low dental-carries-inducibility.

Example B-4

Custard cream

Five hundred parts by weight of corn starch, 500 parts by weight of a saccharide powder prepared by the method in Example A-1, 400 parts by weight of sucrose, and 5 parts by weight of salt were sufficiently mixed by passing them through a sieve, and added with 1,400 parts by weight of egg. The mixture was stirred, gradually added with 5,000 parts by weight of boiling milk, and further continued stirring while hanging the resultant mixture over a slow fire. When the corn starch in the resultant mixture was completely gelatinized to give the whole content semi-transparent, the fire was put off, and the resultant mixture was cooled and added with a small amount of a vanilla flavor to obtain a custard cream.

The product has a smooth surface and gloss, as well as having a moderate sweetness and taste.

Example B-5

Chocolate

Forty parts by weight of cacao paste, 10 parts by weight of cacao butter, and 50 parts by weight of a saccharide powder prepared by the method in Example A-4 were mixed, and the mixture was passed though a refiner to lower the particle size, transferred to a conche, and kneaded up at 50° C. over 2 days.

Before completion of the processing, 0.5 parts by weight of lecithin was added to the mixture and sufficiently dispersed therein.

The resultant mixture was adjusted to 31° C. with a thermoregulator, poured into a mold just before the solidification of butter, deaerated with a vibrator, and passed through a tunnel kept at 10° C. for 20 minutes to effect solidification. The resultant solid was removed from the mold and packaged to obtain the captioned product.

The product having a non-hygroscopicity, as well as a satisfiable color, gloss and texture, smoothly melts in the mouth to exhibit a satisfactory quality and moderate taste.

The product can be advantageously used as a chocolate having a relatively-low dental-carries-inducibility.

Example B-6

Chewing gum

Twenty-five parts by weight of gum base and 40 parts by weight of a panose-rich saccharide powder prepared by the method in Example A-2 were sufficiently kneaded at 60° C., and the mixture was successively admixed with 30 parts by weight of a saccharide powder prepared by the method in Example A-2, 1.5 parts by weight of calcium phosphate, 0.1 part by weight of an l-menthol inclusion complex with β-cyclodextrin, and a small amount of a seasoning. The resultant mixture was further kneaded sufficiently, subjected to a roll processing, and cut into the captioned product.

The product is a satisfactory chewing gum having a relatively-low dental-carries-inducibility.

Example B-7

Powdered juice

Thirty-three parts by weight of a powdered orange-juice was sufficiently mixed under stirring conditions with 60 parts by weight of a saccharide powder prepared by the method in Example A-2, 0.6 parts by weight of anhydrous citric acid, 0.1 part by weight of malic acid, 0.1 part by weight of L-ascorbic acid, 0.1 part by weight of sodium citrate, 0.6 parts by weight of a flavoring powder, and 0.5 parts by weight of pullulan, and the resultant mixture was fed to a fluidized-bed granulator adjusted at an emission temperature of 40° C. and an airflow rate of 150 m³/min, and sprayed thereto a panose-rich saccharide solution prepared by the method in Example A-2 as a coating agent or a binder at a rate of 100 ml/min for 30 minutes to effect granulation, followed by recovering a powdered juice.

The product containing 30% orange juice, d.s.b., was free of solidification and unsatisfactory taste and smell, as well as being stable for a relatively-long period of time.

Example B-8

Uiro-no-moto

To 90 parts by weight of rice powder was admixed to homogeneity 20 parts by weight of corn starch, 120 parts by weight of a saccharide powder prepared by the method in Example A-5, and 4 parts by weight of pullulan to obtain a uiro-no-moto.

Two hundred g of the product and one g of matcha were admixed to homogeneity with water, transferred to a container and steamed for 60 minutes to obtain a matcha uiro.

The product had a satisfactory gloss, biting property and taste. The deterioration of starch in the product was also prevented and the product was stable for a relatively-long period of time.

Example B-9

Bettara-zuke-no-moto

Four parts by weight of a saccharide powder prepared by the method in Example A-3, 0.05 parts by weight of a licorice preparation, 0.008 parts by weight of malic acid, 0.07 parts by weight of sodium glutamate, 0.03 parts by weight of potassium sorbate, and 0.2 parts by weight of pullulan were mixed to homogeneity to obtain the captioned product.

Thirty kg of a Japanese radish was in an usual manner successively picked with salt, sugar and a seasoning prepared with 4 kg of the bettara-zuke-no-moto to obtain a bettara-zuke.

The product having a satisfactory color, gloss and flavor, as well as an adequate sweetness and biting property, was stable for a relatively-long period of time without substantially exhibiting acidification.

Example B-10

Tablet

Fifty parts by weight of acetylsalicylic acid was sufficiently mixed with 14 parts by weight of a saccharide powder prepared by the method in Example A-4, and 4 parts by weight of corn starch, and the resultant mixture was in an usual manner tabletted with a tabletting machine to obtain tablets, 680 mg each.

The product has a substantial non-hygroscopicity and sufficient physical-strength, as well as a relatively-high degradability in water.

[Effect of the invention]

As evident from above, the present panose-rich saccharide powder having 48–93% panose, d.s.b., together with other oligosaccharides, as well as having a crystallinity of 19% or higher, has a substantial non-hygroscopicity and a satisfactory stability and free-flowing ability. Thus, the present saccharide powder completely diminishes the drawbacks of conventional non-crystalline panose-rich saccharides, i.e. a relatively-high hygroscopicity which readily causes both solidification and loss of free-flowing ability.

Since the present saccharide powder having 48–93% panose, d.s.b., and a crystallinity of 19% or higher is readily handleable, it reduces by a large margin material- and labor-costs in the care of packaging, transportation and storage.

The present saccharide powder can be advantageously used in the fields wherein conventional saccharide powders have been used, as well as in other fields such as mixed sweetener, chocolate, chewing gum, powdered juice and tablet wherein the application of conventional saccharide powders has been deemed very difficult.

While there has been described what is at present considered to be the preferred embodiments of the invention, it will be understood the various modifications may be made therein, and it is intended to cover in the appended claims all such modifications as fall within the true spirits and scope of the invention.

We claim:

1. A powdery saccharide composition comprising 48–93 w/w % panose and at least 7% oligosaccharide, on a dry solid basis, said oligosaccharide selected from the group consisting of maltose, isomaltose, maltotriose, isomaltotriose, isomaltosyl maltose, tetraoligosaccharide, higher oligosaccharides, and mixtures thereof, said saccharide composition exhibiting a crystallinity of 19% or higher and predominant diffraction angles (2Θ) of 16.4°, 18.2°, 18.5° and 20.8° on X-ray powder diffraction analysis.

2. A process for preparing a powdery saccharide composition, which comprises:

crysallizing a solution containing 45–93 w/w % panose and at least 7% oligosaccharide, based on the weight of the dry solid, to form a massecuite in the presence of a seed crystal of panose, said oligosaccharide being selected from the group consisting of maltose, isolmaltose, maltotriose, isomaltotriose, isomaltosyl maltose, tetraoligosaccharide, higher oligosaccharides, and mixtures thereof;

pulverizing the massecuite; and recovering the resultant powdery saccharide composition which exhibits a crystallinity of 19% or higher and predominant diffraction angles (2Θ) of 16.4°, 18.2°, 18.5° and 20.8° on x-ray powder diffraction analysis.

3. The process of claim 2, wherein the total concentration of said solid in said solution is in the range of about 70–95 w/w %.

4. The process of claim 2, wherein said solution is prepared by fractionating a saccharide solution containing panose together with monosaccharides and oligosaccharides on a column chromatograph using a strongly-acidic cation exchange resin, collecting a panose-rich fraction containing 45–93 w/w % panose and at least 7% of oligosaccharide on a dry solid basis, and concentrating the panose-rich fraction.

* * * * *